(12) United States Patent
Schlun et al.

(10) Patent No.: US 9,155,642 B2
(45) Date of Patent: Oct. 13, 2015

(54) BEND-CAPABLE TUBULAR PROSTHESIS

(71) Applicant: C. R. Bard, Inc., Murray Hill, NJ (US)

(72) Inventors: Martin Schlun, Herxheim Bei Landau/Pfalz (DE); Achim Zipse, Baden-Baden (DE); Thilo Wack, Durmersheim (DE); Andreas Block, Lubeck (DE)

(73) Assignee: C.R. Bard, Inc., Murray Hill, NJ (US)

( * ) Notice: Subject to any disclaimer, the term of this patent is extended or adjusted under 35 U.S.C. 154(b) by 333 days.

(21) Appl. No.: 13/849,312

(22) Filed: Mar. 22, 2013

(65) Prior Publication Data

US 2013/0218260 A1    Aug. 22, 2013

Related U.S. Application Data

(63) Continuation of application No. 12/300,985, filed as application No. PCT/EP2007/004407 on May 16, 2007, now Pat. No. 8,403,978.

(30) Foreign Application Priority Data

May 17, 2006    (WO) .................. PCT/EP07/04407

(51) Int. Cl.
*A61F 2/06* (2013.01)
*A61F 2/89* (2013.01)
(Continued)

(52) U.S. Cl.
CPC ... *A61F 2/89* (2013.01); *A61F 2/91* (2013.01); *A61F 2/915* (2013.01);
(Continued)

(58) Field of Classification Search
CPC ... A61F 2/82; A61F 2/89; A61F 2002/91508; A61F 2/06; A61F 2/91

USPC .................................. 623/1.15, 1.42
See application file for complete search history.

(56) References Cited

U.S. PATENT DOCUMENTS

| 5,091,205 A | 2/1992 | Fan |
| 5,464,419 A | 11/1995 | Glastra |

(Continued)

FOREIGN PATENT DOCUMENTS

| DE | 04130431 A1 | 3/1993 |
| DE | 29621207 U1 | 1/1997 |

(Continued)

OTHER PUBLICATIONS

U.S. Appl. No. 10/362,040, filed Jun. 27, 2003 Office Action dated Aug. 2, 2006.

(Continued)

*Primary Examiner* — Victor Nguyen
(74) *Attorney, Agent, or Firm* — Buchalter Nemer, PLC

(57) ABSTRACT

A tubular prosthesis having a succession of turns around a longitudinal axis includes connectors between adjacent turns distributed around the circumference of the prosthesis. Each turn includes struts interspersed by inflection zones located at the axial ends of each turn such that, when the prosthesis expands radially, gaps open up between adjacent struts of each of the turn. The inflection zones are distributed regularly around the circumference so that the gaps are substantially the same size as each other around the circumference of the turn. The prosthesis may include a turn that exhibits a stagger zone within which the gap between adjacent struts is of an individual size different from that common to the other gaps of that turn. The inflection zones in that turn that lie circumferentially next to the stagger zone are displaced out of facing relationship with corresponding zones of inflection in the adjacent turn.

5 Claims, 4 Drawing Sheets

(51) Int. Cl.
*A61F 2/91* (2013.01)
*A61F 2/915* (2013.01)

(52) U.S. Cl.
CPC ............... *A61F 2002/91508* (2013.01); *A61F 2002/91516* (2013.01); *A61F 2002/91525* (2013.01); *A61F 2002/91533* (2013.01); *A61F 2002/91558* (2013.01); *A61F 2230/0054* (2013.01); *A61F 2250/0029* (2013.01)

(56) References Cited

U.S. PATENT DOCUMENTS

| | | |
|---|---|---|
| 5,527,353 A | 6/1996 | Schmitt |
| 5,591,223 A | 1/1997 | Lock et al. |
| 5,645,532 A | 7/1997 | Horgan |
| 5,725,572 A | 3/1998 | Lam et al. |
| 5,741,327 A | 4/1998 | Frantzen |
| 5,759,192 A | 6/1998 | Saunders |
| 5,800,511 A | 9/1998 | Mayer |
| 5,824,042 A | 10/1998 | Lombardi et al. |
| 5,824,059 A | 10/1998 | Wijay |
| 5,824,077 A | 10/1998 | Mayer |
| 5,843,118 A | 12/1998 | Sepetka et al. |
| 5,858,556 A | 1/1999 | Eckert et al. |
| 5,861,027 A | 1/1999 | Trapp |
| 5,868,783 A | 2/1999 | Tower |
| 5,922,020 A * | 7/1999 | Klein et al. ............. 623/1.15 |
| 6,022,374 A | 2/2000 | Imran |
| 6,053,940 A | 4/2000 | Wijay |
| 6,056,187 A | 5/2000 | Acciai et al. |
| 6,086,611 A | 7/2000 | Duffy et al. |
| 6,099,561 A | 8/2000 | Alt |
| 6,174,329 B1 | 1/2001 | Callol et al. |
| 6,241,762 B1 | 6/2001 | Shanley |
| 6,270,524 B1 | 8/2001 | Kim |
| 6,293,966 B1 | 9/2001 | Frantzen |
| 6,312,456 B1 | 11/2001 | Kranz et al. |
| 6,334,871 B1 | 1/2002 | Dor et al. |
| 6,355,057 B1 | 3/2002 | DeMarais et al. |
| 6,379,381 B1 | 4/2002 | Hossainy et al. |
| 6,387,123 B1 | 5/2002 | Jacobs et al. |
| 6,409,752 B1 | 6/2002 | Boatman et al. |
| 6,451,047 B2 | 9/2002 | McCrea et al. |
| 6,471,721 B1 | 10/2002 | Dang |
| 6,475,233 B2 | 11/2002 | Trozera |
| 6,478,816 B1 | 11/2002 | Kveen et al. |
| 6,540,777 B2 | 4/2003 | Stenzel et al. |
| 6,547,818 B1 | 4/2003 | Rourke et al. |
| 6,562,065 B1 | 5/2003 | Shanley |
| 6,585,757 B1 | 7/2003 | Callol |
| 6,605,110 B2 | 8/2003 | Harrison |
| 6,629,994 B2 | 10/2003 | Gomez et al. |
| 6,676,700 B1 | 1/2004 | Jacobs et al. |
| 6,770,089 B1 | 8/2004 | Hong et al. |
| 6,797,217 B2 | 9/2004 | McCrea et al. |
| 6,827,734 B2 | 12/2004 | Fariabi |
| 6,878,162 B2 | 4/2005 | Bales et al. |
| 6,979,346 B1 | 12/2005 | Hossainy et al. |
| 7,060,093 B2 | 6/2006 | Dang et al. |
| 7,135,038 B1 | 11/2006 | Limon |
| 7,175,654 B2 | 2/2007 | Bonsignore et al. |
| 7,381,217 B2 | 6/2008 | Tischler |
| 7,462,190 B2 | 12/2008 | Lombardi |
| 7,468,071 B2 | 12/2008 | Edwin et al. |
| 7,479,157 B2 | 1/2009 | Weber et al. |
| 7,691,461 B1 | 4/2010 | Prabhu |
| 7,771,463 B2 | 8/2010 | Ton et al. |
| 7,772,659 B2 | 8/2010 | Rodmacq et al. |
| 8,043,364 B2 | 10/2011 | Lombardi et al. |
| 8,152,842 B2 | 4/2012 | Schlun |
| 8,292,950 B2 | 10/2012 | Dorn et al. |
| 8,322,593 B2 | 12/2012 | Wack |
| 8,403,978 B2 | 3/2013 | Schlun et al. |
| 8,475,520 B2 | 7/2013 | Wack et al. |
| 8,500,793 B2 | 8/2013 | Zipse et al. |
| 8,518,101 B2 | 8/2013 | Dreher |
| 8,551,156 B2 | 10/2013 | Wack et al. |
| 2002/0007212 A1 | 1/2002 | Brown et al. |
| 2002/0116044 A1 | 8/2002 | Cottone et al. |
| 2002/0116051 A1 | 8/2002 | Cragg |
| 2002/0138136 A1 | 9/2002 | Chandresekaran et al. |
| 2002/0193867 A1 | 12/2002 | Gladdish et al. |
| 2002/0193869 A1 | 12/2002 | Dang |
| 2002/0198589 A1 | 12/2002 | Leong |
| 2003/0055485 A1 | 3/2003 | Lee et al. |
| 2003/0135254 A1 | 7/2003 | Curcio et al. |
| 2003/0144725 A1 | 7/2003 | Lombardi |
| 2003/0216807 A1 | 11/2003 | Jones et al. |
| 2003/0225448 A1 | 12/2003 | Gerberding |
| 2004/0015228 A1 | 1/2004 | Lombardi et al. |
| 2004/0015229 A1 | 1/2004 | Fulkerson et al. |
| 2004/0034402 A1 | 2/2004 | Bales et al. |
| 2004/0044401 A1 | 3/2004 | Bales et al. |
| 2004/0073290 A1 * | 4/2004 | Chouinard ............. 623/1.15 |
| 2004/0073291 A1 | 4/2004 | Brown et al. |
| 2004/0088043 A1 * | 5/2004 | Klein ..................... 623/1.16 |
| 2004/0117002 A1 | 6/2004 | Girton et al. |
| 2004/0230293 A1 | 11/2004 | Yip et al. |
| 2004/0236400 A1 | 11/2004 | Edwin et al. |
| 2004/0236409 A1 | 11/2004 | Pelton et al. |
| 2004/0254637 A1 | 12/2004 | Yang et al. |
| 2005/0049682 A1 | 3/2005 | Leanna et al. |
| 2005/0060025 A1 | 3/2005 | Mackiewicz et al. |
| 2005/0149168 A1 | 7/2005 | Gregorich |
| 2005/0172471 A1 | 8/2005 | Vietmeier |
| 2005/0182477 A1 | 8/2005 | White |
| 2005/0184277 A1 | 8/2005 | Su et al. |
| 2005/0222667 A1 | 10/2005 | Hunt |
| 2005/0278019 A1 | 12/2005 | Gregorich |
| 2006/0030934 A1 | 2/2006 | Hogendijk et al. |
| 2006/0064153 A1 | 3/2006 | Langhans et al. |
| 2006/0216431 A1 | 9/2006 | Kerrigan |
| 2006/0241741 A1 | 10/2006 | Lootz |
| 2006/0253187 A1 | 11/2006 | Moriuchi et al. |
| 2006/0265049 A1 | 11/2006 | Gray et al. |
| 2007/0112421 A1 | 5/2007 | O'Brien |
| 2007/0219624 A1 | 9/2007 | Brown et al. |
| 2008/0051885 A1 | 2/2008 | Llanos et al. |
| 2008/0188924 A1 | 8/2008 | Prabhu |
| 2009/0125092 A1 | 5/2009 | McCrea et al. |
| 2009/0125099 A1 | 5/2009 | Weber et al. |
| 2009/0200360 A1 | 8/2009 | Wack |
| 2009/0204201 A1 | 8/2009 | Wack |
| 2009/0204203 A1 | 8/2009 | Allen et al. |
| 2009/0264982 A1 | 10/2009 | Krause et al. |
| 2010/0016949 A1 | 1/2010 | Wack |
| 2010/0070021 A1 | 3/2010 | Wack et al. |
| 2010/0114298 A1 | 5/2010 | Dorn et al. |
| 2010/0191321 A1 | 7/2010 | Schlun et al. |
| 2010/0204784 A1 | 8/2010 | Molaei et al. |
| 2010/0211161 A1 | 8/2010 | Dreher |
| 2010/0234936 A1 | 9/2010 | Schlun |
| 2010/0249903 A1 | 9/2010 | Wack et al. |
| 2010/0298921 A1 | 11/2010 | Schlun et al. |
| 2011/0196473 A1 | 8/2011 | McCrea et al. |
| 2011/0198327 A1 | 8/2011 | Prabhu |
| 2011/0245905 A1 | 10/2011 | Weber et al. |
| 2011/0319977 A1 | 12/2011 | Pandelidis et al. |
| 2012/0041542 A1 | 2/2012 | Lombardi et al. |

FOREIGN PATENT DOCUMENTS

| | | |
|---|---|---|
| DE | 19728337 A1 | 1/1999 |
| DE | 29904817 U1 | 5/1999 |
| DE | 10201151 A1 | 7/2003 |
| DE | 202004014789 U1 | 1/2005 |
| DE | 102004045994 A1 | 3/2006 |
| EP | 0481365 A1 | 4/1992 |
| EP | 0709068 A2 | 5/1996 |
| EP | 0800800 A1 | 10/1997 |
| EP | 0847733 A1 | 6/1998 |
| EP | 0870483 A2 | 10/1998 |
| EP | 1029517 A2 | 8/2000 |
| EP | 1034751 A2 | 9/2000 |

(56) References Cited

FOREIGN PATENT DOCUMENTS

| | | | |
|---|---|---|---|
| EP | 1157673 | A2 | 11/2001 |
| EP | 1190685 | A2 | 3/2002 |
| EP | 1212991 | A2 | 6/2002 |
| EP | 1245203 | A2 | 10/2002 |
| EP | 1255507 | A1 | 11/2002 |
| EP | 1356789 | A1 | 10/2003 |
| EP | 1433438 | A2 | 6/2004 |
| EP | 1488763 | A2 | 12/2004 |
| EP | 1767240 | A1 | 3/2007 |
| EP | 2134301 | A2 | 12/2009 |
| FR | 2626046 | A1 | 7/1989 |
| GB | 453944 | A | 9/1936 |
| JP | 07315147 | A | 12/1995 |
| JP | 2004-506477 | A | 3/2004 |
| JP | 2007-504891 | A | 3/2007 |
| JP | 4827965 | B2 | 11/2011 |
| JP | 4933018 | B2 | 5/2012 |
| WO | 9417754 | A1 | 8/1994 |
| WO | 9503010 | A1 | 2/1995 |
| WO | 9626689 | A1 | 9/1996 |
| WO | 9733534 | A1 | 9/1997 |
| WO | 9820810 | A1 | 5/1998 |
| WO | 9915108 | A2 | 4/1999 |
| WO | 9938457 | A1 | 8/1999 |
| WO | 9949928 | A1 | 10/1999 |
| WO | 9955253 | A1 | 11/1999 |
| WO | 0045742 | A1 | 8/2000 |
| WO | 0049971 | A1 | 8/2000 |
| WO | 0064375 | A1 | 11/2000 |
| WO | 0132102 | A1 | 5/2001 |
| WO | 0158384 | A1 | 8/2001 |
| WO | 0176508 | A2 | 10/2001 |
| WO | 0101889 | A1 | 11/2001 |
| WO | 0215820 | A2 | 2/2002 |
| WO | 0249544 | A1 | 6/2002 |
| WO | 03055414 | A1 | 7/2003 |
| WO | 03075797 | | 9/2003 |
| WO | 03101343 | A1 | 12/2003 |
| WO | 2004019820 | A1 | 3/2004 |
| WO | 2004028408 | A1 | 4/2004 |
| WO | 2004032802 | A2 | 4/2004 |
| WO | 2004058384 | A1 | 7/2004 |
| WO | 2005067816 | A1 | 7/2005 |
| WO | 2005072652 | A1 | 8/2005 |
| WO | 2005104991 | A1 | 11/2005 |
| WO | 2005032403 | A3 | 12/2005 |
| WO | 2006010636 | A1 | 2/2006 |
| WO | 2006010638 | A1 | 2/2006 |
| WO | 2006014768 | A1 | 2/2006 |
| WO | 2006025847 | A2 | 3/2006 |
| WO | 2006036912 | A2 | 4/2006 |
| WO | 2006047977 | A1 | 5/2006 |
| WO | 2006064153 | A1 | 6/2006 |
| WO | 2007073413 | A1 | 6/2007 |
| WO | 2006026778 | A3 | 11/2007 |
| WO | 2007131798 | A1 | 11/2007 |
| WO | 2007135090 | A1 | 11/2007 |
| WO | 2008006830 | A1 | 1/2008 |
| WO | 2008022949 | A1 | 2/2008 |
| WO | 2008022950 | A1 | 2/2008 |
| WO | 2008025762 | A1 | 3/2008 |
| WO | 2008028964 | A2 | 3/2008 |
| WO | 2008055980 | A1 | 5/2008 |
| WO | 2008068279 | A1 | 6/2008 |
| WO | 2008101987 | A1 | 8/2008 |
| WO | 2008119837 | A2 | 10/2008 |
| WO | 2009030748 | A2 | 3/2009 |

OTHER PUBLICATIONS

U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Non-Final Office Action dated Mar. 15, 2012.
U.S. Appl. No. 12/300,985, filed Aug. 6, 2010 Notice of Allowance dated Nov. 16, 2012.
U.S. Appl. No. 12/301,019, filed Feb. 2, 2009 Advisory Action dated Apr. 27, 2011.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/373,116, filed Jul. 14, 2009 Advisory Action dated Jul. 26, 2011.
U.S. Appl. No. 12/373,116, filed Jul. 14, 2009 Examiner's Answer dated Jan. 3, 2013.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,102, filed Feb. 19, 2009 Non-Final Office Action dated Nov. 15, 2010.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/438,527, filed Feb. 23, 2009 Advisory Action dated May 24, 2012.
U.S. Appl. No. 12/438,527, filed Feb. 23, 2009 Final Office Action dated Mar. 7, 2012.
U.S. Appl. No. 12/438,527, filed Feb. 23, 2009 Non-Final Office Action dated Jul. 11, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/514,177, filed May 8, 2009 Advisory Action dated Sep. 10, 2012.
U.S. Appl. No. 12/514,177, filed May 8, 2009 Final Office Action dated Apr. 27, 2011.
U.S. Appl. No. 12/514,177, filed May 8, 2009 Final Office Action dated Jul. 11, 2012.
U.S. Appl. No. 12/514,177, filed May 8, 2009 Non-Final Office Action dated Jan. 5, 2011.
U.S. Appl. No. 12/514,177, filed May 8, 2009 Non-Final Office Action dated Mar. 13, 2012.

(56) References Cited

OTHER PUBLICATIONS

U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Non-Final Office Action dated May 6, 2011.
U.S. Appl. No. 12/517,096, filed Jun. 1, 2009 Non-Final Office Action dated Nov. 28, 2012.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated Dec. 17, 2010.
U.S. Appl. No. 12/594,531, filed Oct. 2, 2009 Non-Final Office Action dated May 12, 2011.
U.S. Appl. No. 12/594,531, filed Oct. 2, 2009 Non-Final Office Action dated Oct. 2, 2012.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 09177588 filed Aug. 14, 2007 Search Report dated Aug. 12, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2001/009467 International Preliminary Examination Report Sep. 17, 2002.
PCT/EP2001/009467 International Search Report dated Feb. 18, 2002.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.
PCT/EP2007/057041 filed Jul. 10, 2007 Written Opinion Jan. 10, 2009.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/058416 filed Aug. 14, 2007 International Preliminary Report on Patentability dated Feb. 24, 2009.
PCT/EP2007/058416 filed Aug. 14, 2007 International Search Report dated Nov. 22, 2007.
PCT/EP2007/058416 filed Aug. 14, 2007 Written Opinion dated Feb. 23, 2009.
PCT/EP2007/058912 filed on Aug. 28, 2007 International Preliminary Report on Patentability dated Nov. 5, 2008.
PCT/EP2007/058912 filed on Aug. 28, 2007 Search Report dated Nov. 12, 2007.
PCT/EP2007/058912 filed on Aug. 28, 2007 Written Opinion dated Nov. 12, 2007.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/062155 filed on Nov. 9, 2007 Search Report dated Mar. 12. 2008.
PCT/EP2007/062155 filed on Nov. 9, 2007 Written Opinion dated Mar. 12, 2009.
PCT/EP2007/062155 filed on Novermber 9, 2007 International Preliminary Report on Patentability dated Oct. 15, 2008.
PCT/EP2007/063347 filed Dec. 5, 2007 Search Report dated Jun. 10, 2009.
PCT/EP2007/063347 filed Dec. 5, 2007 Written Opinion mailed Jun. 10, 2009.
PCT/EP2007/063347 filed on Dec. 5, 2007 Search Report mailed Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.
U.S. Appl. No. 13/279,189, filed Oct. 21, 2011 Non-Final Office Action dated Oct. 17, 2012.
PCT/EP2007/054822 filed May 16, 2007 International Preliminary Report on Patentability dated Nov. 18, 2008.
U.S. Appl. No. 12/301,019, filed Feb. 2, 2009 Notice of Allowance dated Jul. 9, 2013.
U.S. Appl. No. 12/438,102, filed Feb. 19, 2009 Final Office Action dated Apr. 21, 2011.
U.S. Appl. No. 12/438,102, filed Feb. 19, 2009 Advisory Action dated Jul. 12, 2011.
U.S. Appl. No. 12/438,102, filed Feb. 19, 2009 Notice of Allowance dated Dec. 6, 2011.
U.S. Appl. No. 12/438,527, filed Feb. 23, 2009 Non-Final Office Action dated Oct. 9, 2014.
U.S. Appl. No. 12/438,527, filed Feb. 23, 2009 Final Office Action dated May 14, 2015.
U.S. Appl. No. 12/440,415, filed Mar. 6, 2009 Notice of Allowance dated Apr. 3, 2013.
U.S. Appl. No. 12/514,177, filed May 8, 2009 Notice of Allowance dated Jun. 13, 2013.

(56) References Cited

OTHER PUBLICATIONS

U.S. Appl. No. 12/517,096, filed Jun. 1, 2009 Notice of Allowance dated Mar. 18, 2013.
U.S. Appl. No. 12/528,289, filed Aug. 26, 2009 Notice of Allowance dated Jun. 29, 2012.
U.S. Appl. No. 12/594,531, filed Oct. 2, 2009 Notice of Allowance dated May 7, 2013.
U.S. Appl. No. 13/279,189, filed Oct. 21, 2011 Final Office Action dated May 2, 2013.
U.S. Appl. No. 13/279,189, filed Oct. 21, 2011 Notice of Allowance dated May 6, 2014.
U.S. Appl. No. 13/402,787, filed Feb. 22, 2012 Notice of Allowance dated Apr. 9, 2013.
U.S. Appl. No. 14/045,603, filed Oct. 3, 2013 Non-Final Office Action dated Dec. 15, 2014.
U.S. Appl. No. 14/045,603, filed Oct. 3, 2013 Notice of Allowance dated Mar. 30, 2015.
U.S. Appl. No. 13/975,147, filed Aug. 23, 2013 Non-Final Office Action dated May 15, 2014.
U.S. Appl. No. 13/975,147, filed Aug. 23, 2013 Notice of Allowance dated Feb. 11, 2015.
U.S. Appl. No. 12/676,584, filed Mar. 4, 2010 Non-Final Office Action dated May 24, 2013.

* cited by examiner 10  12  14  16  18  12

10  18  16  20  $D_1$  $D_2$  12  14  PRIOR ART $C_e$

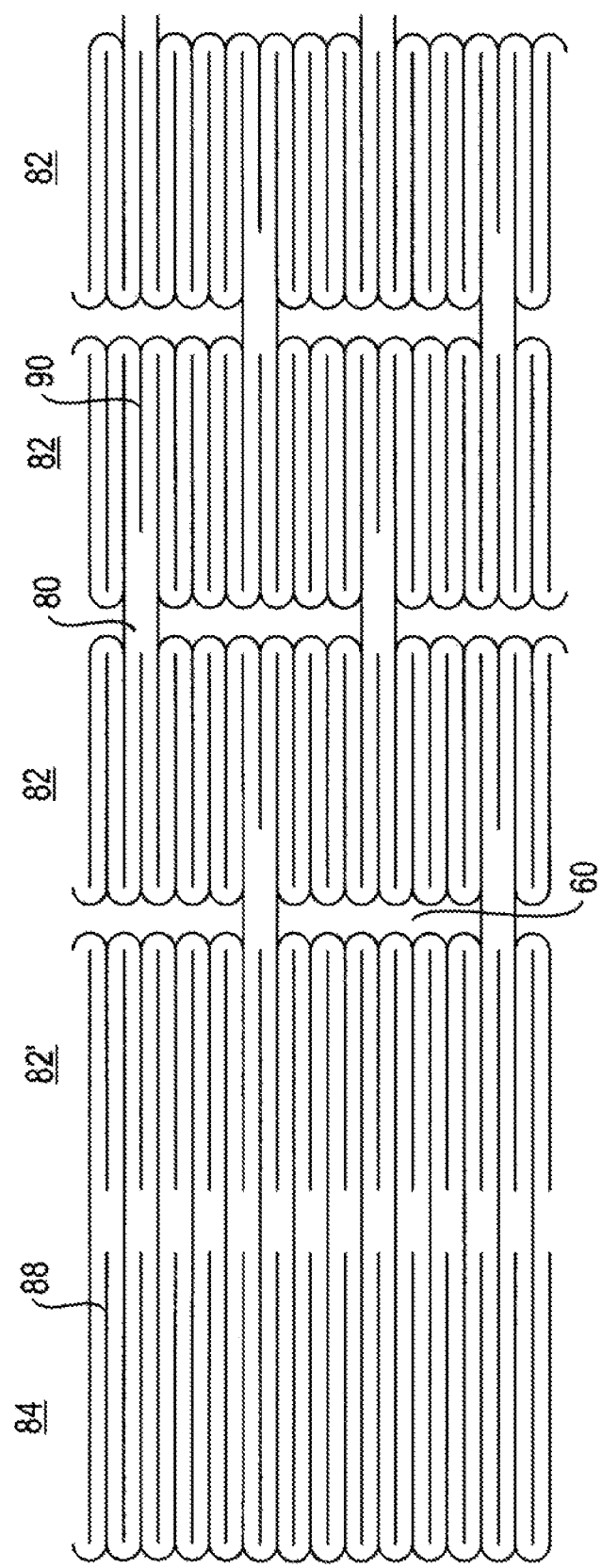

BEND-CAPABLE TUBULAR PROSTHESIS

PRIORITY

This application is a continuation of U.S. patent application Ser. No. 12/300,985, filed as a U.S. national stage application under 35 USC §371 of International Application No. PCT/EP2007/004407, filed May 16, 2007, now U.S. Pat. No. 8,403,978, which claims priority to United Kingdom Patent Application No. 0609841.2, filed May 17, 2006, each of which is incorporated by reference in its entirety into this application.

TECHNICAL FIELD

This invention relates to tubular medical prostheses that are expandable from a radially compact disposition to a radially expanded disposition. In the compact disposition, the prosthesis can by delivered to its operational site in the body, typically trans-luminally and percutaneously, using a delivery system which is a sort of catheter. Exemplary of this class of prosthesis is a nickel titanium shape memory alloy stent for a bodily lumen which is often but not always an arterial lumen. See for example the disclosure of applicant's earlier WO 01/32102.

BACKGROUND

Bodily soft tissue is remarkably flexible and needs generally to be flexible. It is difficult for a metal stent to match bodily tissue for flexibility. WO 01/32102 is concerned with flexibility of the stent during its journey, from outside the body to the operational site within the body, as for example the catheter delivery system advances along a tortuous path from the point of entry in the body. However, there is also a need for metal stents (and other prostheses) that are destined to be installed at a location in the body where severe bending is to be expected. If the prosthesis could be made more tolerant of severe bending after placement, that would be attractive to doctors and their patients.

WO 01/32102 shows what could be termed a "classic" self-expanding stent structure of zig-zag stenting rings composed of struts interspersed by points of inflection and with adjacent stenting rings linked axially by connector portions. In the compact delivery disposition of the stent (FIG. 3 of WO 01/32102) the struts of the zig-zag rings are more or less parallel to each other so that each point of inflection represents a change of direction for the material of the stenting ring of more or less 180°. As the stent expands to its deployed configuration (FIG. 4 of WO 01/32102) the radius of the stenting ring expands by movement of the struts away from each other so that gaps open up between adjacent struts, and the adjacent points of inflection move further apart (but nevertheless remain spaced at equal intervals to each other around the circumference of the stenting ring).

The connectors serve to restrain relative circumferential movement of the zig-zag rings relative to each other. Thus, if the points of inflection of adjacent stenting rings are facing each other in the compact delivery disposition of the stent, as in WO 01/32102, then so will be these points of inflection still facing each other in the expanded disposition of the stent. When an expanded stent is subject, in the body, to extreme bending, so that the longitudinal axis of the stent is no longer a straight line but a pronounced curve (as in a banana), then the facing points of inflection on the inside of the bend approach each other. The more extreme the bending, the closer the facing points of inflection become until, in the end, these facing "peaks" abut each other or rub past each other.

Any such abutment or rubbing is undesirable. One way to guard against it is to choose a stent design that can be classified as a "peak-to-valley" design rather than a "peak-to-peak" design as seen in applicant's WO 01/32102. The art is replete with suggestions for peak-to-valley designs in which the peaks of any one zig-zag stenting ring do not face corresponding peaks of the next adjacent stenting ring but, instead, are circumferentially offset to the peaks of the next adjacent stenting ring by half of the gap between two adjacent peaks of the same ring, in the expanded disposition of the stent. Then, under extreme bending, any particular peak on the inside of the bend can advance into the V-shaped space between two peaks of the next adjacent stenting ring, without any abutment or rubbing on any portion of the material of the next adjacent stenting ring.

The present invention is concerned with the above-explained problem. It seeks to improve the in situ bend capability of stents including those seen in WO 01/32102. However, the invention also seeks to achieve this performance enhancement without sacrificing other attractive qualities of stents such as disclosed in WO 01/32102. For example, simplicity of modelling of stress distributions within the stent is attractive in the management of fatigue performance of metal stents. Manufacturing simplicity of course facilitates management of cost which should improve access to stents, for those people who need them.

Looking at WO 01/32102, one can quickly see that performance in extreme bending could be enhanced by extending the length of the portions that connect adjacent zig-zag stenting rings. The longer these "bridges" then the more the stent can bend without abutment of peaks on the inside of the bend. However, large axial gaps between adjacent stenting rings are not desirable, for then the tissue of the lumen that is being stented by the prosthesis is relatively unsupported, at least between adjacent stenting rings.

For the same reason, one seeks as far as possible to distribute the metallic material of the stent as evenly as possible over the length and circumference of the tubular envelope of the stent so that support for the stented tissue is as even and uninterrupted as possible. This of course indicates that all gaps between all adjacent struts and points of inflection of the stent matrix should be as constant as possible. Generally, one does not modulate the strut matrix of a stent, over the length and circumference of the stent, to suit tissue variations within the stenting site. Generally, one does not seek to place a particular point on the circumference of the stent in opposition to a particular zone of tissue within the stenting site. For these reasons alone, one seeks a stent matrix that is everywhere the same over the length and circumference of the prosthesis.

In principle, the problem addressed in the present invention, and the solution here disclosed, is useful in all classes of stenting prostheses. That is to say, it works with a stent matrix that exhibits the (spiral) turns around the axis of a helical stent, as well as with a stent that features a stack of endless stenting rings. It works with balloon-expandable stents and resilient self-expanding stents as well as with nickel titanium shape memory alloy stents.

SUMMARY

Nevertheless, according to the present invention, it is contemplated to depart from the prior good design practice, and deliberately configure the stent matrix so that it is locally different, at one point at least, around the circumference of at least every second stenting ring within the prosthesis. In short, we envisage within each stenting ring at least one location (we call it a "stagger zone") where the gap between adjacent points of inflection is smaller (but it could be greater) than the otherwise constant (or near constant) "wavelength" around the circumference of the prosthesis for that particular stenting ring.

It will be appreciated that, for any particular pair of adjacent stenting rings, even just one such abnormal gap (stagger zone) could be enough to set up a circumferential offset between the otherwise facing "peak-to-peak" points of inflection that we see in, for example, FIG. 4 of WO 01/32102. In practice, however, a design with only one stagger zone on the circumference might not be enough to deliver the desired circumferential offset all around the circumference, especially in designs that feature a large number of struts, in any one turn around the axis of the prosthesis. Four stagger zones are likely to be enough. Designs with two, three or four such zones are presently preferred, but up to 6 stagger zones per turn are readily conceivable, the more so with stent design with a notably small mesh size in their matrix.

As mentioned above, it is the connectors between adjacent stenting rings that prevent adjacent stenting rings from rotating around the long axis of the prosthesis relative to each other and thereby preserve the designed intended relationship between facing stenting rings and their respective points of inflection. Generally, it will be convenient to incorporate the design variation that creates the abnormal gap between adjacent points of inflection with the design of the connector zone between two adjacent turns. Thus, in perhaps the simplest case, we can envisage a connector from which two struts extend into a stenting ring or turn on one side of the connector, and two other struts extend in the other axial direction, into the next adjacent stenting ring or turn. If the angle between the first two struts is "normal" for that stenting ring, but the angle between the opposite pair of struts, in the other of the two stenting rings, is much smaller than "normal", then the points of inflection circumferentially on either side of the connector, that would be facing each other in the classic construction of WO 01/32102, will be circumferentially offset from each other, because of the different angle of the struts each side of the connector. Think of the connector as the trunk of a human body, with the legs of the body slightly open and the two arms of the body. Imagine the angle between the upwardly outstretched arms significantly greater than the angle between the legs.

Rather than set out a string of statements of invention, and then repeat them in a set of claims, we opt for economy of text, refrain from reciting statements of invention, and present various aspects of the above explained inventive concept in claims appended to this description.

We have stated that setting up a "peak-to-valley" configuration of otherwise facing inflection zones is conveniently incorporated in the design of portions that connect adjacent stenting rings (or helical turns). However, one can readily envisage that the necessary offset can be created in a stagger zone that is circumferentially spaced from connectors. There is no imperative that the stagger zone must be coincident with the connector zone.

It will be evident that a stagger zone can be created in a number of different ways. One can locally manipulate the mechanical properties of the material of the stagger zone, not just be local modulation of the dimensions of the inflection points or struts within the stagger zone, relative to the rest of the circumference of the stenting ring, but could also contemplate manipulation of the mechanical properties of the material in the stagger zone by local heat treatment or even chemical treatment. It is even possible to envisage adding components to an otherwise "classic" stenting ring structure as in WO 01/32102, such as a flexible "tie" between the two struts that are destined to deliver a smaller than usual gap between adjacent points of inflection. When a painter erects an easel, there is a "piece of string" that runs between the front frame of the easel, and the rear strut of the easel, not far above the ground, where the gap between the front legs of the easel and the single rear leg of the easel rest on the ground. A classic stent such as shown in WO 01/32102 could be modified by inclusion in it of judiciously placed "pieces of string" from biologically compatible material, in order to restrain two adjacent struts of selected stenting rings of the prosthesis from opening to the full extent that occurs for all the other struts of that particular stenting ring. (We mention this possibility not with any expectation that it will be a preferred construction, but in the recognition that competitors stimulated by the present disclosure might be obliged to turn to such constructions in the hope of avoiding the inventive concept of the present application). The motto "keep it simple" is rather powerful and the present inventors are proud of a contribution to the art that is essentially simple but should deliver a powerful enhancement of performance.

At this juncture, it is worth noting that a shape memory alloy stent is given its "remembered" configuration by a heat treatment. In the case of WO 01/32102, that heat treatment is given with the points of inflection arranged "peak-to-peak". With shape memory alloy stents embodying the present invention, however, the heat treatment is with the inflection points arranged as intended, therefore, not peak to peak, but in the circumferentially staggered arrangement brought about by the stagger zone(s).

In the context of the present invention, attention is directed to the disclosure of US/2004/0073290 and, in particular, drawings FIGS. 4 and 5 and the associated text. We see adjacent zig-zag stenting rings with points of inflection that are more or less "peak-to-peak" in the compact configuration of drawing FIG. 4, but not so much peak-to-peak in the expanded configuration of drawing FIG. 5. However, the struts of any particular zig-zag stenting ring are not all the same length. Some are relatively long, some are relatively short, and some are of intermediate length. By contrast, it appears that the angle that opens up between any two struts that diverge from any particular point of inflection is always the same, so that any technical effect of circumferential displacement of peak-to-peak points of inflection is accomplished not by local variation of an angle between two adjacent struts but, rather, by modulations of the length of adjacent struts in each of the stenting rings. Putting it another way, each connector portion 24 is the intersection of two straight lines in the form of an "X" shape and this is not what is envisaged with the present invention.

Thinking about the bend capability of any particular stent design, this might be limited by peak to peak abutment on the inside of the (banana) bend but could also be restricted by incipient buckling of the stent matrix at some point on the matrix. Clearly, to obtain benefit from the present invention, the stent matrix to which it is to be applied must be capable of bending without buckling, to the extent needed to bring the benefits of the present invention into play. In general, the sparser the population of connectors, the more capacity the lattice will have to bend without buckling.

BRIEF DESCRIPTION OF THE DRAWINGS

For a better understanding of the present invention, and to show more clearly how the same may be carried into effect, reference will now be made, by way of example, to the accompanying drawings, in which:

FIGS. 6 and 7 are corresponding views of a stent structure in accordance with the present invention.

DETAILED DESCRIPTION

FIGS. 1 to 5 give only the most cursory impression of the wealth of stent strut matrix proposals contained within the state of the art. However, they provide enough disclosure to set the advantages of the present invention in the context of relevant prior art.

Figure 1:
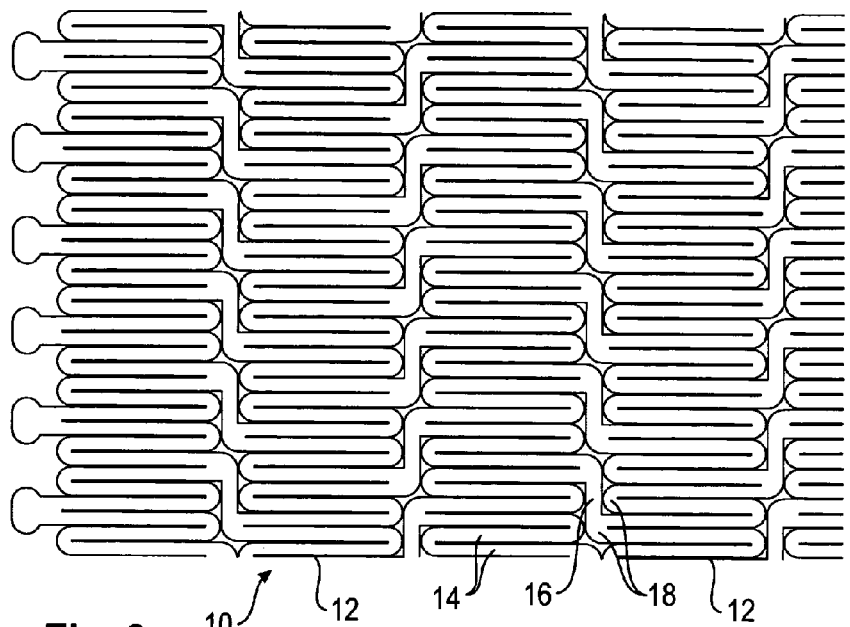
FIGS. 1 and 2 show, respectively content of FIGS. 6 and 2 of US/2003/0055485, being a tubular stent structure opened out flat, seen in plan view, in respectively the radially compact and radially expanded dispositions.
Figure 2:
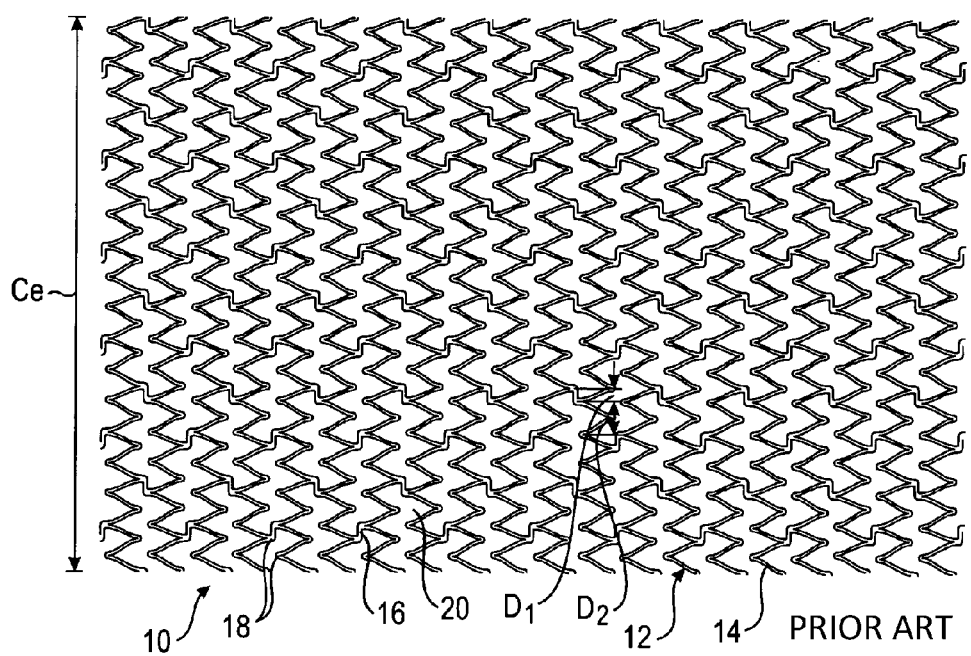

Looking first at FIGS. 1 and 2, we see an example of a stent 10 which utilises circumferential support structures 12 in the form of zig-zag stenting rings. These are spaced apart along the long axis of the stent. They are made up of struts 12 interspersed by points of inflection 18 which US/2003/0055485 designates "apex portions". These apex portions are mostly free to take up positions, in the expanded FIG. 2 disposition of the stent, which are governed only by the stresses transmitted through the struts of that particular stenting ring, or transmitted to that stenting ring by the bodily tissue that presses against it. However, there are also connecting struts 16 each of which joins a selected one of the apex portions of one stenting ring with a selected apex portion of an adjacent stenting ring. From FIG. 1, we see that the connecting struts have length direction that is in the circumferential direction of the stent tube, so that the opposite ends of each particular connecting strut 16 are circumferentially spaced from each other. In the radially compact disposition of FIG. 1, the circumferentially extending connecting strut 16 spans an intervening apex portion between its two ends. However, when the stent expands into its radially expanded configuration represented by FIG. 2, the circumferential length of the connecting strut 16 is not enough to span across an intervening apex portion, because the apex portions arranged around the circumference of any particular stenting ring have moved away from each other by an amount greater than the length of the connecting strut. By selecting a connecting strut length that is approximately half the distance between two adjacent apex portions of the same stenting ring, in the expanded configuration of the stent, one can achieve a "staggering" of the evenly spaced apex portions of one stenting ring, relative to the equal spacing of the apex portions of the next adjacent stenting ring that "faces" the stenting ring of the other end of the connecting strut.

In consequence, when the stent in its expanded configuration is subject to longitudinal compression, or when it is bent sharply (so that its longitudinal axis is not longer straight but arcuate) the facing apex portions on the inside of the bend, or that approach each other as the stent is longitudinally compressed do not butt up against each other but, instead, move into the free gap between two spaced apart apex portions of the other of the two facing stenting rings.

In US/2003/0055485, paragraph 0031, it is stated that the geometry of the stent in the radially compact delivery disposition of FIG. 1 is "highly flexible" so that it can tolerate axial compression on the inside of a bend as described above. Looking at FIG. 1 (FIG. 6 of the US publication) it is not immediately evident how the stated flexibility is provided.

Figure 3:
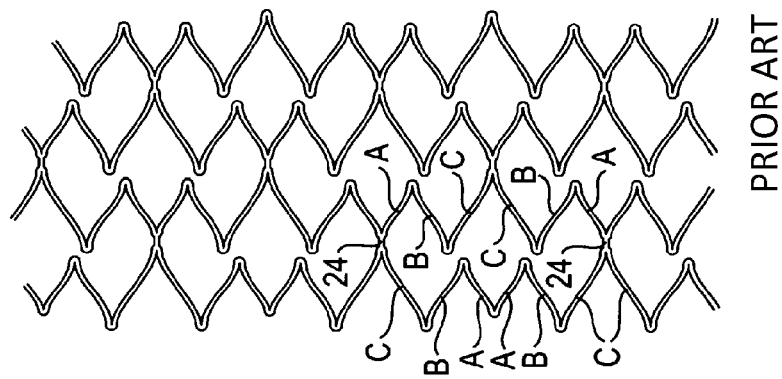
FIG. 3 is a reproduction of FIG. 5 of US/2004/0073290, being a portion of a tubular stent structure, opened out flat, and in a radially expanded configuration.
Figure 5:
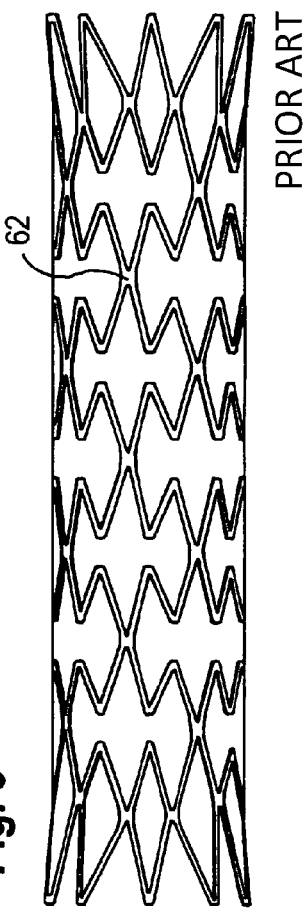

We turn now to FIG. 3, which corresponds to FIG. 5 of US/2004/0073290. In this case, one can see that the connector portions between adjacent zig-zag stenting rings have a very simple construction. They are remarkably short in length but, to the extent that they have a length direction, it is parallel to the longitudinal axis of the stent, rather than in a circumferential direction. Accordingly, there is no circumferential offset between the apex portions facing each other and connected by the connector strut 24.

Nevertheless, we see from FIG. 3, that there is a circumferential offset between unconnected apex portions of adjacent stenting rings.

The offset is accomplished by providing a range of different strut lengths in any particular stenting ring. In particular, each connector 24 is at the apex of a first pair of relatively long struts and a second pair of relatively short struts. Each stenting ring features struts of three different lengths, namely A) short, B) intermediate length and C) long. And we see from FIG. 3 how the strut length progresses around the circumference of each stenting ring in a sequence ABCCBA. We can see how the apex portions at the open end of a bifurcation between two A-struts both fall within a single gap between two C-struts of the adjacent stenting ring. This overlap occurs periodically around the circumference of the prosthesis, on each occasion midway between two adjacent connector portions 24.

In the compact disposition of the stent of FIG. 3, apex portions are "head-to-head" or "peak-to-peak" all the way around the circumference of the stenting cylinder, not just at those locations where a connector portion 24 lies between the head-to-head apex portions. In this respect, there is reduced flexibility in the compact delivery disposition of the stent device, comparable with that of the device of FIG. 1 described above. Again, it is not immediately evident how the device delivers bent flexibility in the compact delivery disposition.

The present applicant specialises in self-expanding stent devices that are formed from a tubular workpiece of nickel titanium shape memory alloy ("NITINOL" trademark). The tube is formed into a stent precursor by forming in it a multiplicity of slits (cut by a laser) that it is convenient to provide all mutually parallel to each other and to the long axis of the tubular workpiece. One such construction can be seen in FIG. 4, this corresponding to FIG. 3 of applicant's earlier publication WO 01/32102, the contents of which are hereby incorporated by reference. Reference to the WO document will reveal how, following laser cutting, portions of the tubular workpiece are removed to leave "holes" in the slitted tube, indicated by reference 60 in FIG. 4. It will be grasped by the skilled reader that provision of these voids in the slitted tube endows the tube, in its delivery system, confined by a sheath that prevents premature self-expansion, greater flexibility for the sheath to advance along a tortuous delivery path to a site of stenting in the body.

Figure 4:
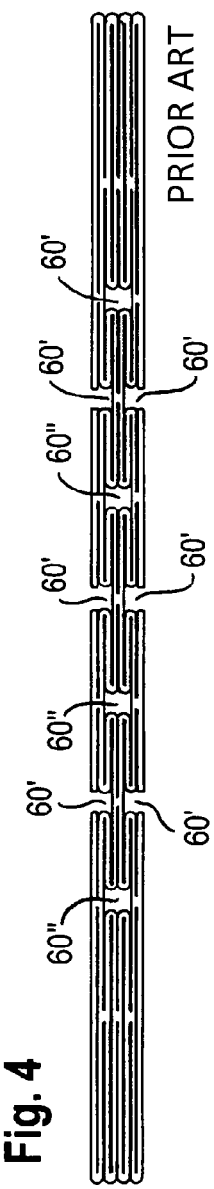
FIGS. 4 and 5 reproduce drawing FIGS. 3 and 4 of applicant's WO 01/32102, being respectively side views of a stent structure in the radially compact and radially expanded dispositions.

FIG. 5 shows the expanded disposition of the FIG. 4 stent construction. A pattern of zig-zag stenting rings connected by short connecting portions 62 can be readily recognised and it can also be seen that the apex portions (here in designated "points of inflection") of adjacent zig-zag stenting rings are facing each other, not only across the connected 62 but also elsewhere around the circumference of the stenting device. Thus, when the expanded stenting device of FIG. 5 is subject to severe lengthwise compressive stress, or severe bending, there is a possibility for facing points of inflection of axially adjacent zig-zag stenting rings to approach each other closely, or even touch on the inside of the bend. The problem being tackled when the present invention was made was how to reduce the likelihood of this adverse event occurring.

One embodiment of the present invention, which does succeed in setting the facing points of inflection of adjacent stenting rings circumferentially offset from each other, will now be described be reference to drawings FIGS. 6 and 7.

FIG. 6 shows a distribution of slits in a tubular workpiece opened out flat, and the similarity with the slit distribution of FIG. 4 is immediately apparent. Note that FIG. 4 is a view from the side of the workpiece, and does not show the workpiece opened out flat whereas FIG. 6 shows the entire circumference of the tubular workpiece, laid out flat on the page. We see from FIG. 6 that there are two connecting struts 80 connecting any two adjacent stenting rings 82. We see at the left-hand end of FIG. 6 the terminal stenting ring 84 which has a longer slit length and is also evident in FIG. 4. We note that FIG. 4 shows the entire length of the stent whereas FIG. 6 shows only a portion of the length of the stent. Whereas the connectors 80 are interspersed by voids 60 just as in FIG. 4, there are no voids between the increased length end stenting ring 84 and its next adjacent normal length stenting ring 82'. Whereas there are two connector portions 80 between the normal length stenting rings, there are 14 connectors 86 between the end stenting ring 84 and its neighbour 82'.

Noteworthy in FIG. 6 is the pattern of length of the individual slits cut by the laser. In general, the slits have a single length, but there are two exceptions. The first exception is that the slit length is longer at the end of the tubular workpiece, to form the end stenting ring 84. One such slit is marked in FIG. 6 with reference 88. The second exception is the length of the slit that terminates at one end of each connector portion 80. One such slit, of shorter length then the others, is designated in FIG. 6 with reference 90. We need to look at FIG. 7 to appreciate the consequence of short struts 90.

Figure 7:
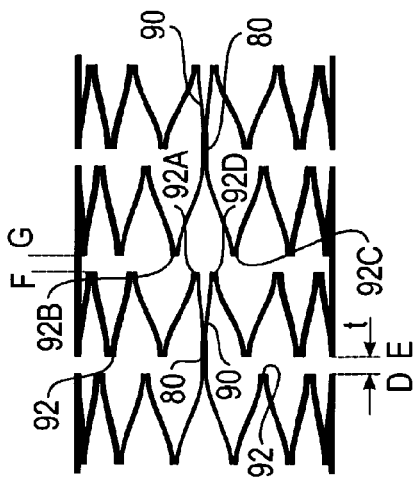

FIG. 7 reveals two of the many connector portions 80. Each connector 80 sits between two adjacent stenting rings at the points of inflection 92 of any one stenting ring are all to be found on a notional circular locus that is transverse to the longitudinal axis of the stent. A gap "t" exists between any particular such circular loci D and E facing each other at periodical intervals down the length of the stent. Within these two circles, we find a circumferential offset between the spaced apart points of inflection 92 in circle E and those of the facing circle D. The offset is found everywhere except at the periodically spaced connectors (in this example there are four) 80.

Turning our attention to the next adjacent pair of facing circles F and G in FIG. 7, the origin of the circumferential offset can be seen in the opposing relationship of the points of inflection 92A, B, C and D. The gap between apex 92B and 92C on the stenting ring that includes circle G is the regular gap between two struts of "normal" length. However, because of the reduced slit length 90, the circumferential gap between points of inflection 92A and 92D is abnormally small so that both points of inflection 92A and 92D "fit" in the normal sized gap between apex 92B and 92C of circle G. In the terminology adopted in the present specification, the zone that includes points of inflection 92A, B, C and D is designated a stagger zone. From FIG. 7 it is immediately evident that providing such a stagger zone by using an abnormally short slit length has a disadvantage, namely, that the gap between points of inflection 92A and 92D is shorter than the regular gaps between other points of inflection spaced around circle F. It hardly need be stated that optimal use of material within a stent matrix calls for a regular matrix of struts, with a minimal amount of material in the radially compact delivery disposition, and a uniformed distribution of that material in the expanded configuration (all gaps the same size) so as to achieve a maximum ratio of expanded diameter to radially compress delivery diameter. Deliberately accepting a plurality of unnecessarily small gaps around the circumference of each stenting ring will have an adverse effect on this ratio of diameters and is therefore not something of itself desirable to stent designers.

Nevertheless, the present invention is attractive, when taken in the context of balancing conflicting constraints on the stent designer. Looking at FIG. 6, one can see the evident simplicity of the stent strut and slit arrangement. The government regulatory authorities impose stringent quality requirements on stent manufacturers. For example, stents must meet stringent metal fatigue requirements. Finite element analysis of stent designs is of crucial importance. A design that is inherently simple should lend itself to reliable prediction of its properties in service. Being able to predict how a stent will perform after it has been installed in a human body is a significant advantage for stent manufacturers that compete to provide the stents most attractive to doctors and medical services.

Figure 8:
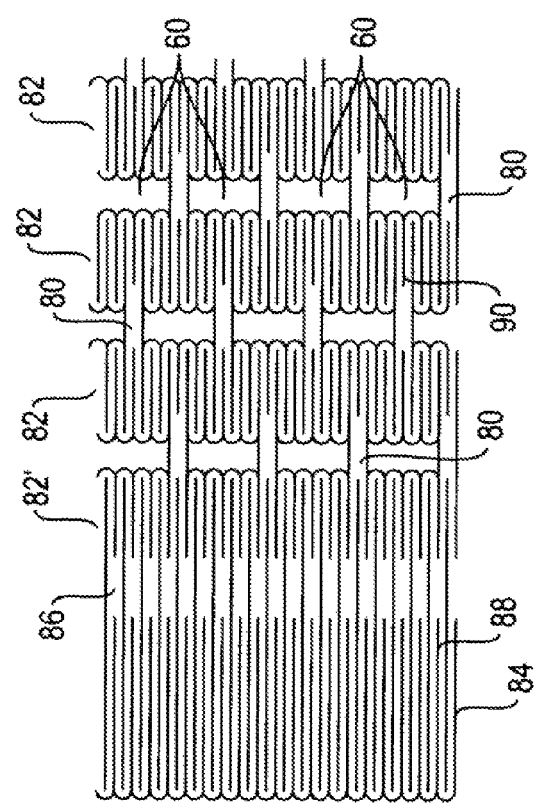
FIGS. 8 and 9 are views corresponding to those of FIGS. 4 and 5, or FIGS. 6 and 7, showing another embodiment of the present invention.
Figure 9:
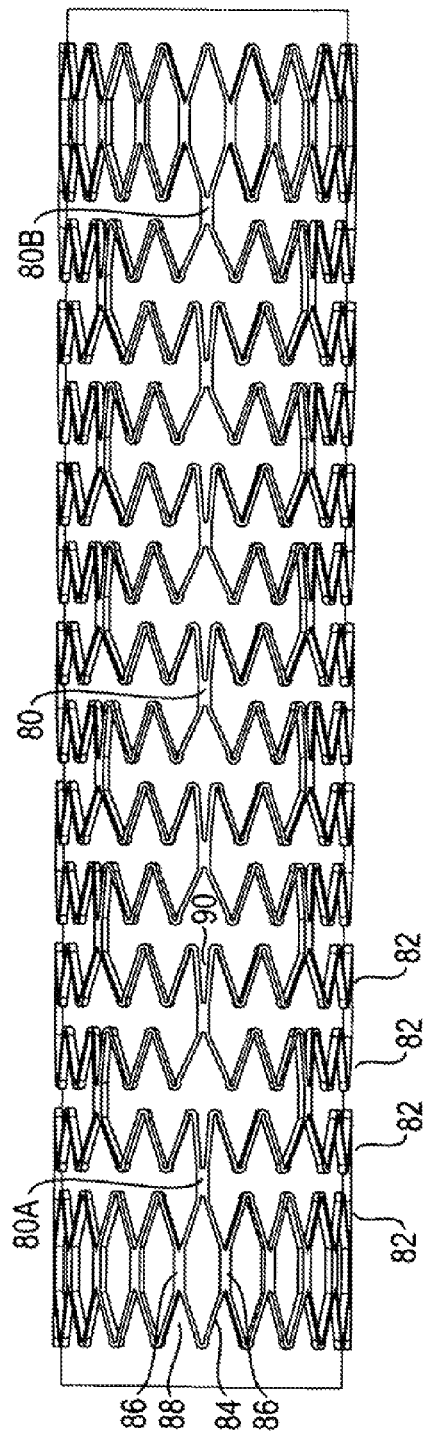

Reference is now made to FIGS. 8 and 9. These have been annotated with references the same as are used in FIGS. 6 and 7, to identify corresponding features. Noteworthy is that there are four connectors rather than two, connecting adjacent stenting rings. Clearly, each stent ring comprises pairs of struts which are unconnected to any pairs of struts of an adjacent stent ring. Further is clear that a number of adjacent stent rings are spaced from each other. FIG. 8 shows the left-hand end of the stent whereas FIG. 9 shows the full length. Actually, the FIG. 9 stent is not the same as the FIG. 8 stent because FIG. 8 shows longer struts in the two end rings but FIG. 9 does not.

In FIG. 9, it is helpful to consider connectors 80A and 80B. The former has the asymmetric shape of all the other connectors of zig-zag rings 82. The latter has an X shape because it is part of the transition from the stagger zone rings 82 to the end ring 84 that lacks any stagger zone. Shown is that the closest end points of a pair of struts of one stent ring and a pair of struts of another stent ring are connected.

The embodiments illustrated in FIGS. 6 to 9 represent only one of a multitude of ways to bring about an angle between struts that is different from the otherwise regular angle between struts around the remainder of the circumference of any particular stenting ring. For example, one could locally modify the material of the stenting ring, either in the points of inflection at one or both ends of the struts that are to form the abnormal size gap, or by judicious modification of the dimensions of those points of inflection or the two struts running between them. Above-mentioned WO 01/32102 contemplates manual removal of individual scrap portions to create voids 60. There are voids 60 in FIG. 6. If manual intervention is to be relied upon to create the voids 60 in an embodiment of the present invention, then it would not be beyond the bounds of imagination to intervene locally, and manually, at portions of the abluminal surface of the workpiece where the properties of the material are to be modified locally in order to deliver a gap of different size, or angle of different size, between two adjacent struts of any particular stenting ring. One envisages that the material could be modified in its composition, by local application of a substance to cause a chemical reaction, or by local application of a substance to modify the microstructure of the material at that point, or by local application of heat or cooling to give the material at that location a different thermal history of that of the material of the remainder of the stenting ring.

In this context, we incorporate, by reference to it, the disclosure of WO2001/076508, from the present applicant, which explains how particular strut configurations can be created by using a jig to hold the workpiece in a particular desired configuration during the heat treatment which "sets" the "remembered" configuration of the struts in the shape memory alloy. Thinking along these lines, one could use instead of struts of different lengths a jig that holds the struts in a configuration such as is shown in FIG. 7, when giving the workpiece its "remembered" configuration, so that it should open up at the stenting site to the remembered disposition even if the length of slit 90 is just the same as the length of all the other slits in the stenting ring.

When thinking of workpieces of every day household dimensions, such as how to prevent a door opening too far, one would use a strut between the door and the frame that has a set length corresponding to the maximum opening that one wishes to impose on the door. In the same way, one could envisage some sort of collapsing tie to impose a maximum size on the gap between points of inflection 92A and 92D, that extends between the respective struts between the slit 90. Of course, stents are very small, but by no means as small as the nanometer dimensions that are in the minds of designers of medical devices, so there seems no justification for dismissing such tie pieces as impracticable. The reality is that, as stent designs become ever more sophisticated, so the range of applications for stents becomes ever greater and, with that, the demand for stents to mimic ever more closely the flexible behaviour of the original bodily tissue, especially when called upon, from time to time, to bend tightly along its length. The challenge is to build a stent that is strong enough to perform the stenting function which is after all the reason for its surgical implantation in the body while, at the same time, rendering the prosthesis as soft and bendy as possible in all other aspects. The present invention makes a valuable contribution to this objective.

Stents need not be made of nickel titanium alloy. Another biologically compatible material familiar to stent designers is stainless steel. Great efforts are currently being made to use other materials such as biologically compatible polymers. All such stents can benefit from the present invention regardless how they are formed. The illustrated embodiments are not limiting.

Stents need not display the same strut matrix over their entire length. We envisage embodiments in which only part of the length of the prosthesis is given the high flexibility of the present invention. Thus, there may be some turns of the stent matrix that include stagger zones, to deliver flexibility, and other parts of the length of the stent (e.g. end zones, or a mid-length portion) where high flexibility is contra-indicated, and so no stagger zones need be provided in these parts of the stent matrix.

What is claimed is:

1. A stent comprising:
   first and second annular frames in alignment with each other to define a longitudinal axis, each annular frame having undulations circumscribing the longitudinal axis, the undulations including a plurality of struts traversing in generally opposed directions to define a plurality of end points disposed generally circumferentially about the longitudinal axis for the respective annular frame, the end points of the first annular frame in facing axial alignment with corresponding end points of adjacent annular frames when the stent is in an unexpanded configuration;
   at least one connector member coupled to a first pair of struts defining one endpoint of the first annular frame and a second pair of struts defining a second endpoint of the second annular frame, the struts of the first annular frame outside of the first pair of struts having generally the same length and the struts of the second annular frame outside of the second pair of struts having generally the same length, the first pair of struts having surfaces exposed to each other to define a first included angle different from a second included angle defined by the exposed surfaces of the second pair of struts so that end points of the first annular frame are offset in a circumferential direction with respect to the corresponding facing end points of an adjacent annular frame in an expanded configuration of the stent;
   and
   a third annular frame in alignment with the first and second annular frames, the third annular frame having undulations circumscribing the longitudinal axis, the undulations including a plurality of struts traversing in generally opposed directions to define a plurality of end points, a second connector member coupled to a third pair of struts defining a third endpoint of the second annular frame and a fourth pair of struts defining a fourth endpoint of the third annular frame, the third pair of struts having surfaces exposed to each other to define a third included angle different from a fourth included angle defined by the exposed surfaces of the fourth pair of struts,
   wherein
   the second included angle is generally the same as the fourth included angle,
   and
   one of the annular frames is connected to a terminal annular frame having closed diamond cells to define a cylinder about the longitudinal axis.

2. The stent according to claim 1, wherein a connector member is disposed between every five struts including the strut connected to the connector member.

3. The stent according to claim 1, wherein the end points of the first annular frame outside of the first pair of struts are generally aligned on a plane orthogonal to the longitudinal axis in both the unexpanded and expanded configurations.

4. The stent according to claim 1, wherein the length of the first annular frame struts are generally the same as the length of the second annular frame struts.

5. The stent according to claim 1, wherein the first annular frame comprises at least two first pair of struts and the second annular frame comprises at least two second pair of struts, wherein a separate connector member connects each of the at least two first pair of struts to a corresponding one of the at least two of the second pair of struts.

* * * * *